United States Patent [19]

Cloud

[11] 4,094,597
[45] June 13, 1978

[54] METHOD AND APPARATUS FOR PRODUCING COMPOSITE FILM IMAGES FOR IDENTIFICATION

[75] Inventor: Don L. Cloud, Springfield, Mo.
[73] Assignee: I.I.C., Inc., Springfield, Mo.
[21] Appl. No.: 723,664
[22] Filed: Sep. 15, 1976
[51] Int. Cl.² .......................................... G03B 21/26
[52] U.S. Cl. ................................................... 353/35
[58] Field of Search .............. 353/35, 30, 26 R, 26 A; 35/28; 242/68.1, 71.1, 71.6; 40/86 A, 95

[56] References Cited

U.S. PATENT DOCUMENTS

| | | | |
|---|---|---|---|
| 2,813,457 | 11/1957 | Fitzgerald | 353/35 |
| 3,336,681 | 8/1967 | Minasy | 353/35 |
| 3,687,536 | 8/1972 | Gorrell et al. | 353/35 |
| 3,975,094 | 8/1976 | Boggs | 353/35 |

*Primary Examiner*—Harry N. Haroian
*Attorney, Agent, or Firm*—Edward J. Cabic

[57] ABSTRACT

A viewing device with a series of image bearing films that are individually positioned to form a composite image. Each film is wound from one roller, past the composite image forming area and onto a take-up roller. In one embodiment a single knob for the entire device operates a drive-chain which is capable of separately engaging the pair of rollers for each film. In another embodiment a control knob and a one-way mechanism is provided for each roller pair to permit the film to be wound precisely back and forth without any binding of the film. The device can be used for facial identification.

24 Claims, 25 Drawing Figures

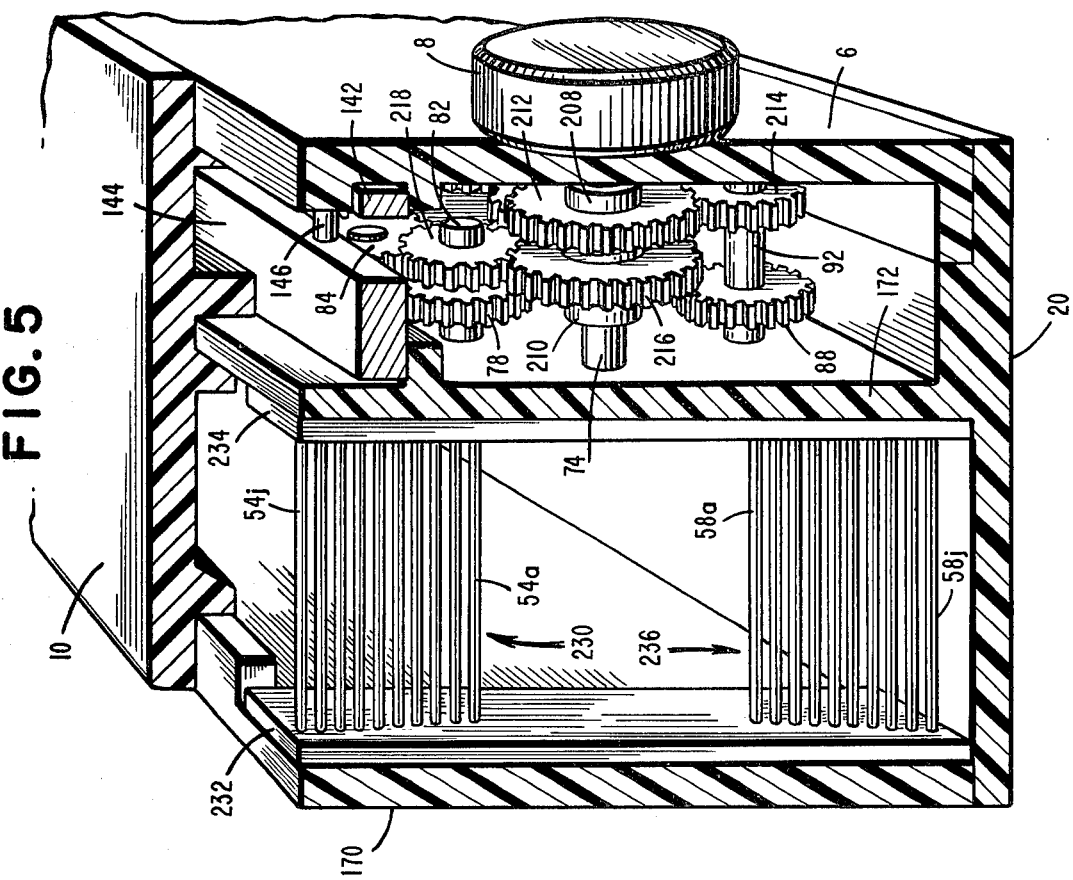
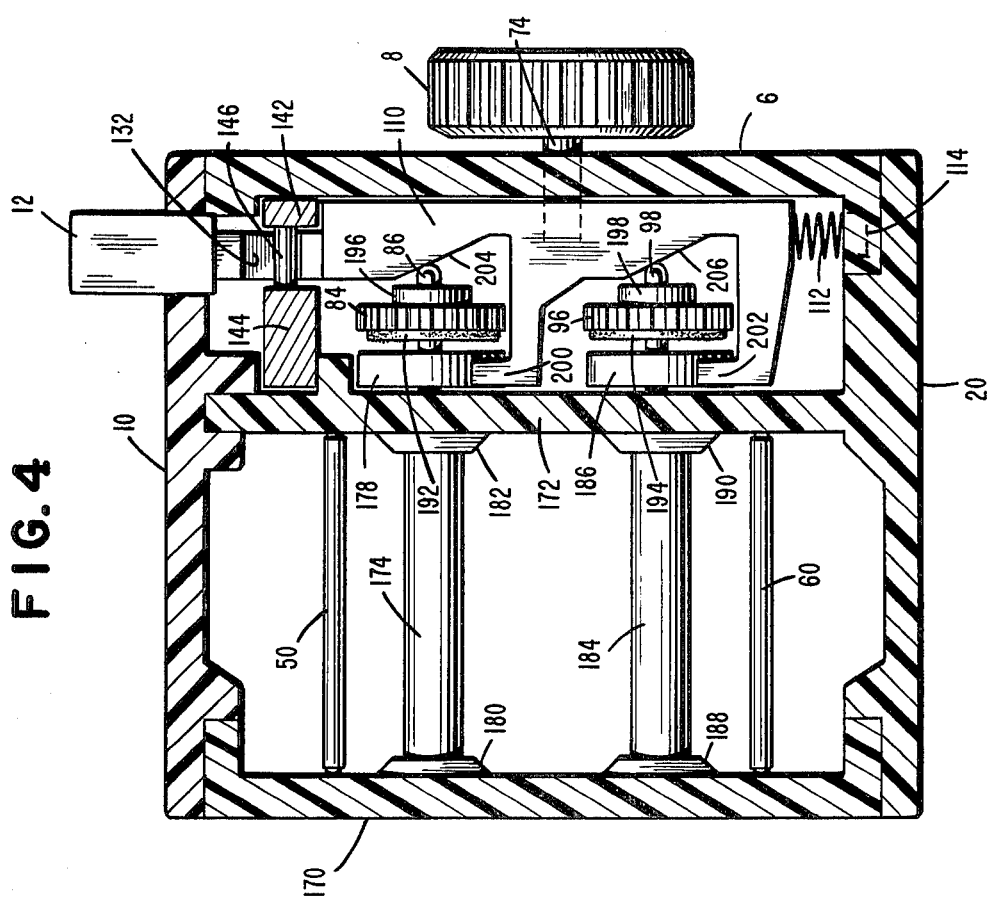

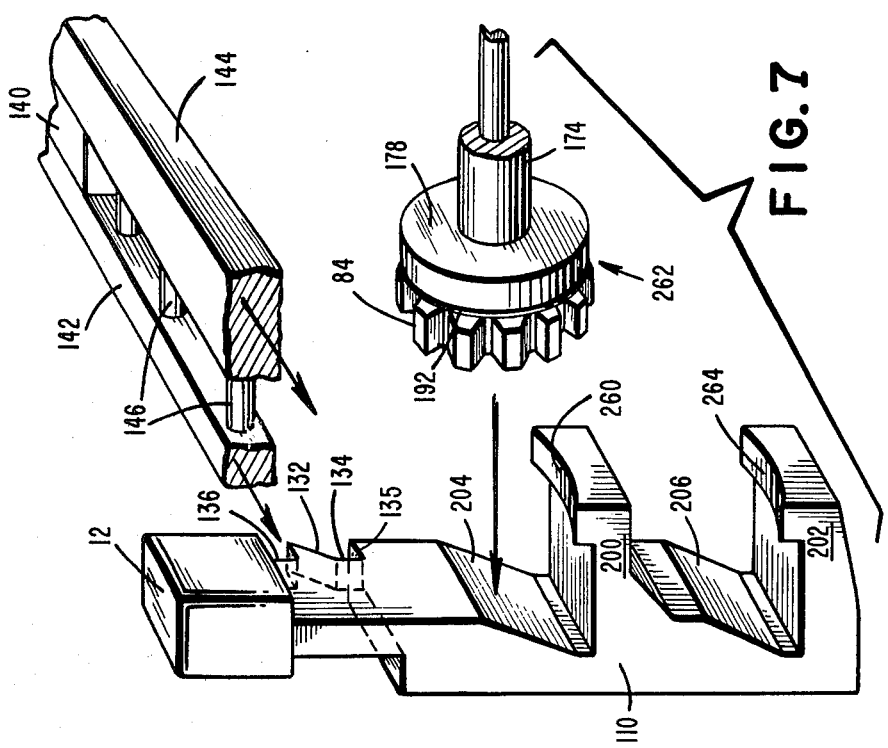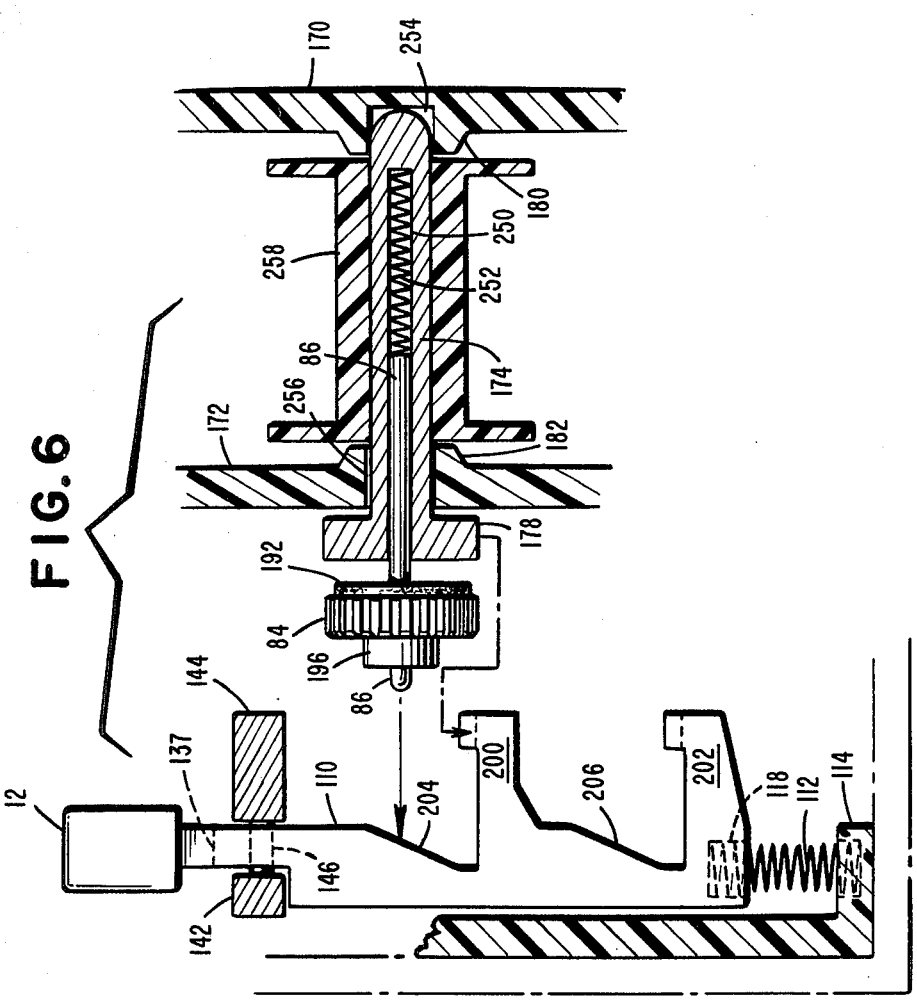

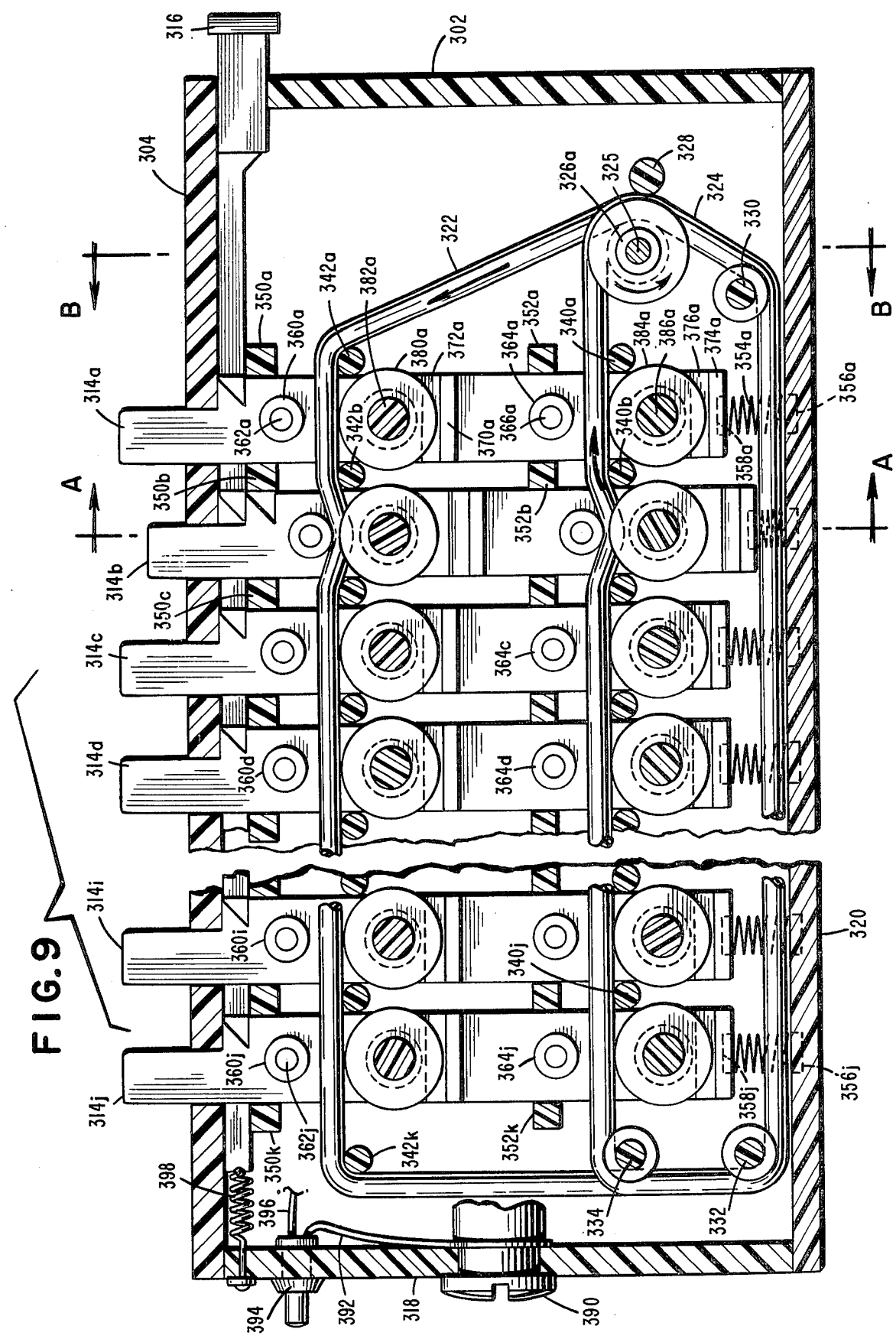

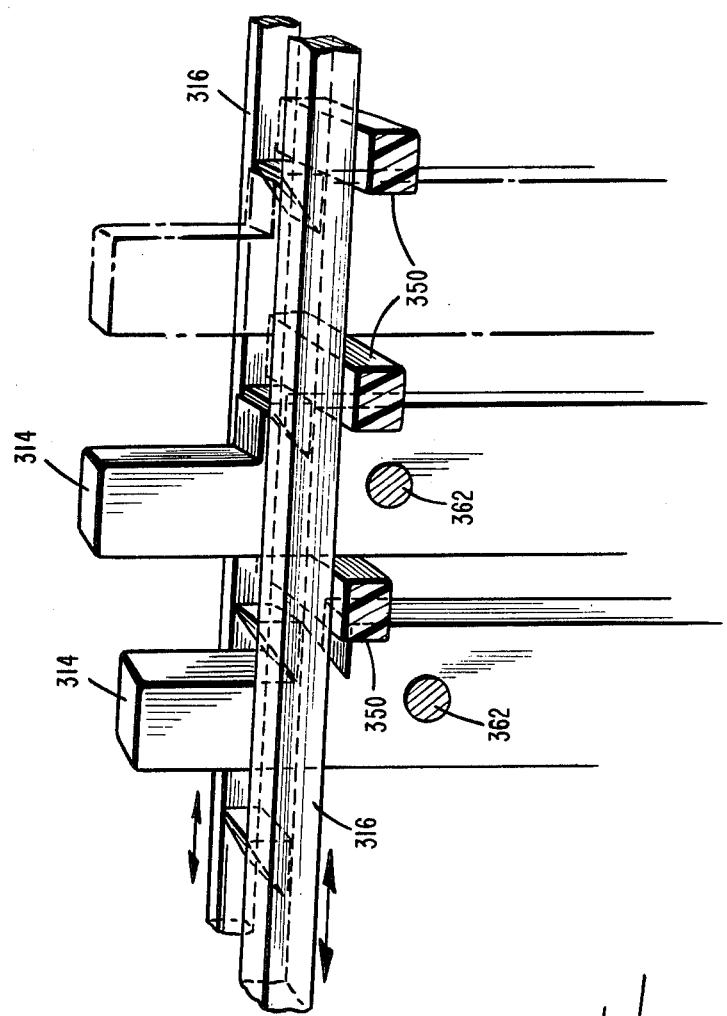
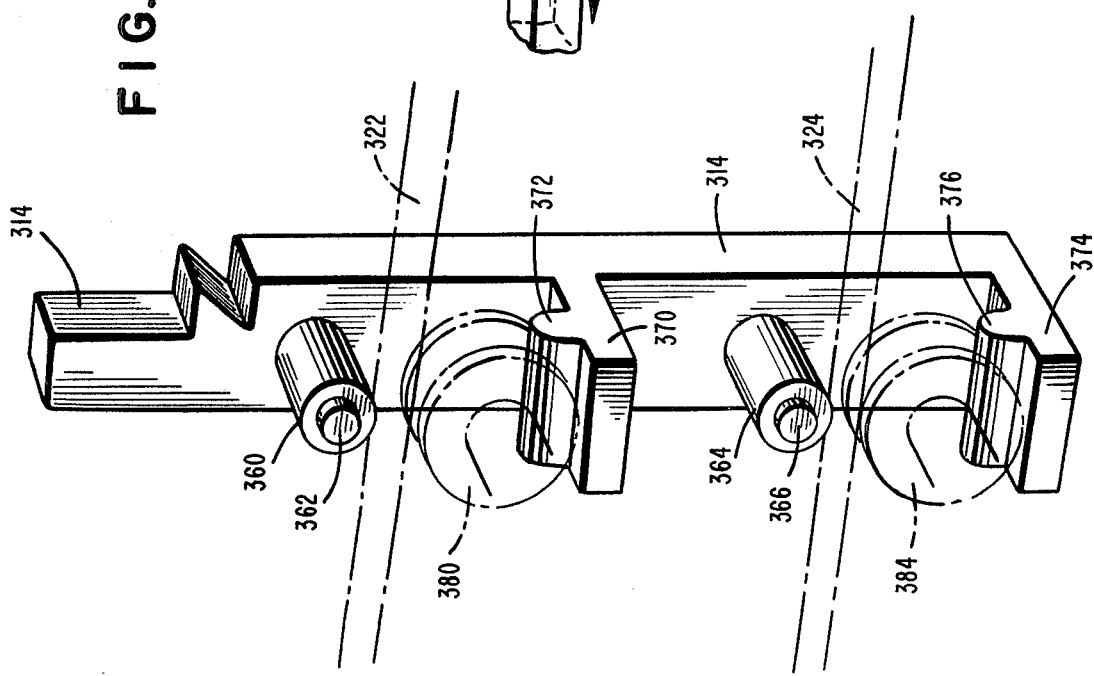

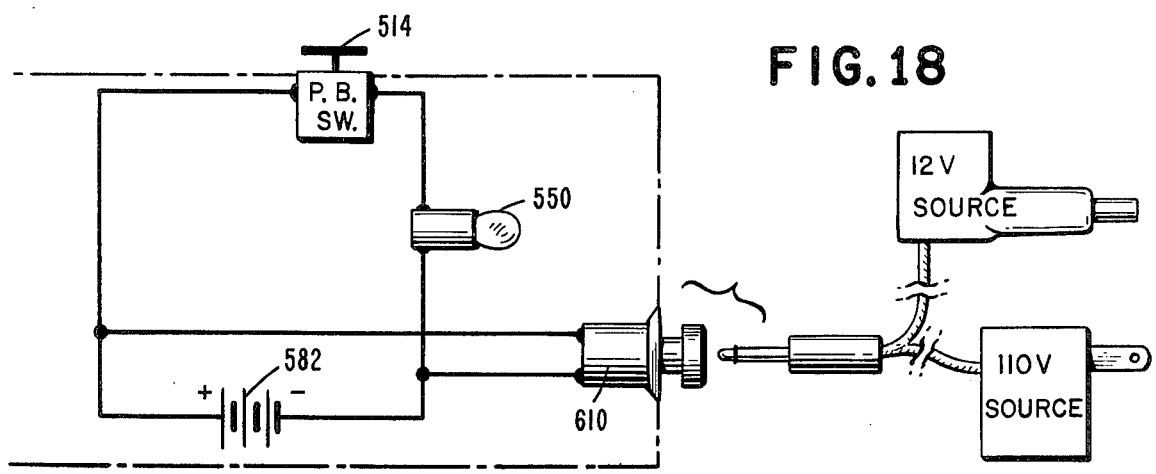
FIG. 18
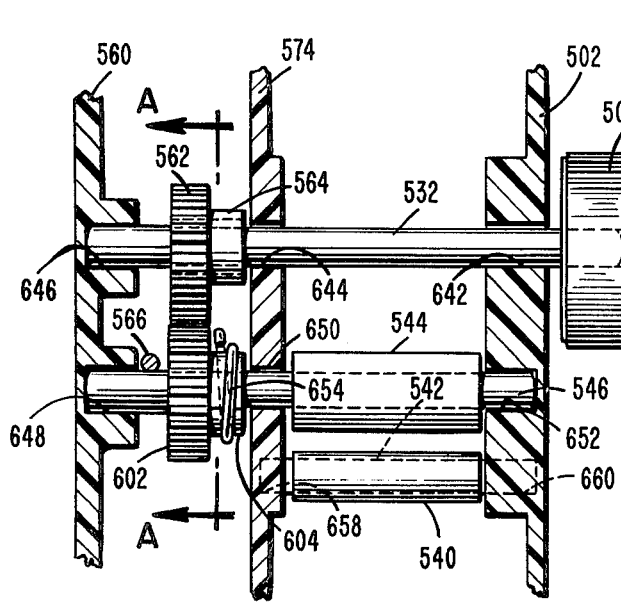
FIG. 19
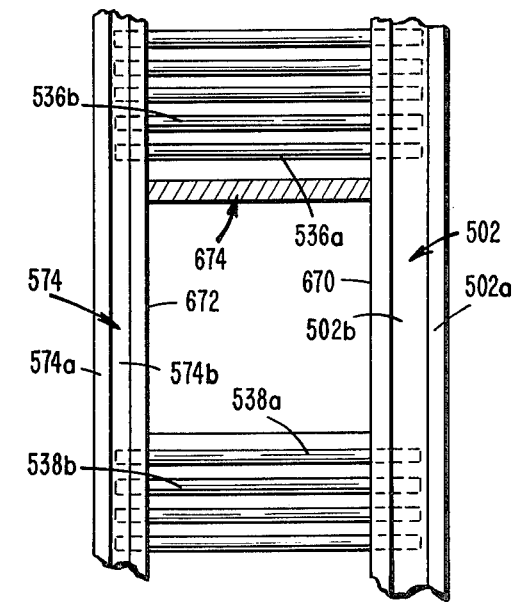
FIG. 20
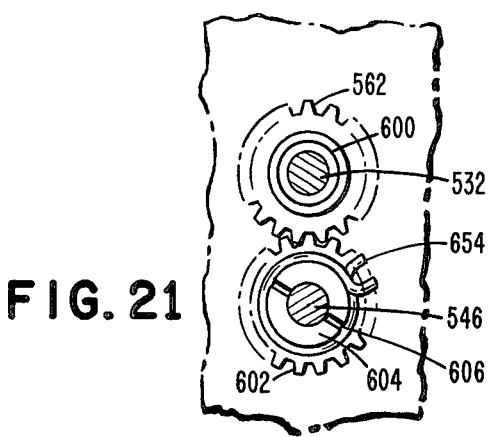
FIG. 21
FIG. 22
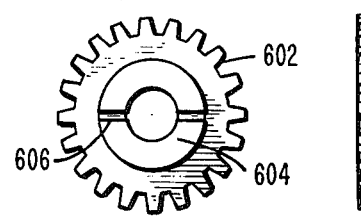
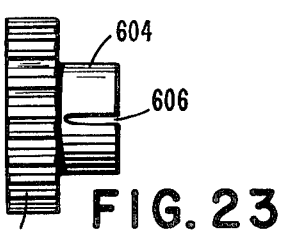
FIG. 23
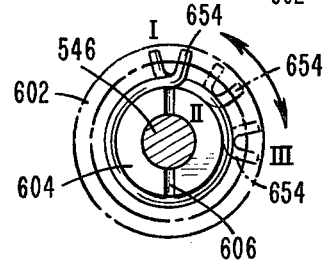
FIG. 24

4,094,597

METHOD AND APPARATUS FOR PRODUCING COMPOSITE FILM IMAGES FOR IDENTIFICATION

BACKGROUND OF THE INVENTION

1. Field of the Invention

The present invention relates to the field of forming composite images by simultaneously superimposing transparent film images. A plurality of films, each containing a separate image characteristic, are superimposed over a lighted viewing area to form a composite image. Various control mechanisms on the outside of the device permit each film strip to be wound from a feed reel past the viewing area and then onto a take-up reel. By rotating the driving control knob in the opposite direction, the film direction is reversed in a trouble-free wind-up procedure without any binding of the film taking place.

2. Description of the Prior Art

The Fitz Gerald Pat. No. 2,813,457 involves a device for overhead projection in which a series of many film layers provide a composite image. This device cannot be handheld.

The Minasy Pat. No. 3,336,681 discloses an image-making device in which a series of elongated strips of relatively thick and stiff transparent photographic film are placed in a vertical holder to form a composite image with each film strip being moved vertically up and down to select the desired image. These straight film strips are not rolled onto spools.

The Gorrell et al Pat. No. 3,687,536 discloses a multi-film projector. Each of the series of upper and lower film spools are connected by a belt drive so that as the upper spool is rotated by its control knob the lower spool will be rotating at the same angular velocity as the upper spool. When there is an unequal amount of film on the two spools, this can cause an accumulative buildup of slack or tension to the film causing problems in holding the film in precise position when other films are rotated over or under it.

SUMMARY OF THE INVENTION

The present invention relates to a viewing device which overcomes the deficiencies of the prior art by utilizing either a single knob control for the entire device or a single control knob for each film spool pair that permits the film to move in a forward or reverse direction without binding. The present construction permits one reel to wind up the film while the other reel of the associated pair is in a free rotating state. A series of overlaying film spools form a composite image which can be used for identification.

BRIEF DESCRIPTION OF THE DRAWINGS

FIG. 4 is a cross-sectional end view of the device shown in FIG. 1.

FIG. 5 is a cross-sectional perspective end view of the device shown in FIG. 1 showing the gear configuration.

FIG. 6 is an exploded view of the mechanism shown in FIG. 4 from the opposite end.

FIG. 7 is a perspective view of the control key engaging mechanism shown in FIG. 6.

FIG. 9 is an internal cross-sectional side view of the device shown in FIG. 8.

FIG. 12 is a perspective view of a control key shown in FIG. 9.

FIG. 13 is a perspective view of the control keys and the upper guide means shown in FIG. 9.

FIG. 18 is a schematic representation of the electrical circuit for the device shown in FIG. 14.

FIG. 19 is a detailed section of a control knob and the associated gears.

FIG. 20 is a detailed section of the front roller combs shown in FIG. 15.

FIG. 21 is a detailed view of the gears taken along line A—A of FIG. 19.

FIG. 22 is an end view of a gear shown in FIG. 21.

FIG. 23 is a side view of the gear shown in FIG. 22.

FIG. 24 is a detailed side view of the lower gear shown in FIG. 21.

DESCRIPTION OF THE PREFERRED EMBODIMENTS

Figure 1:
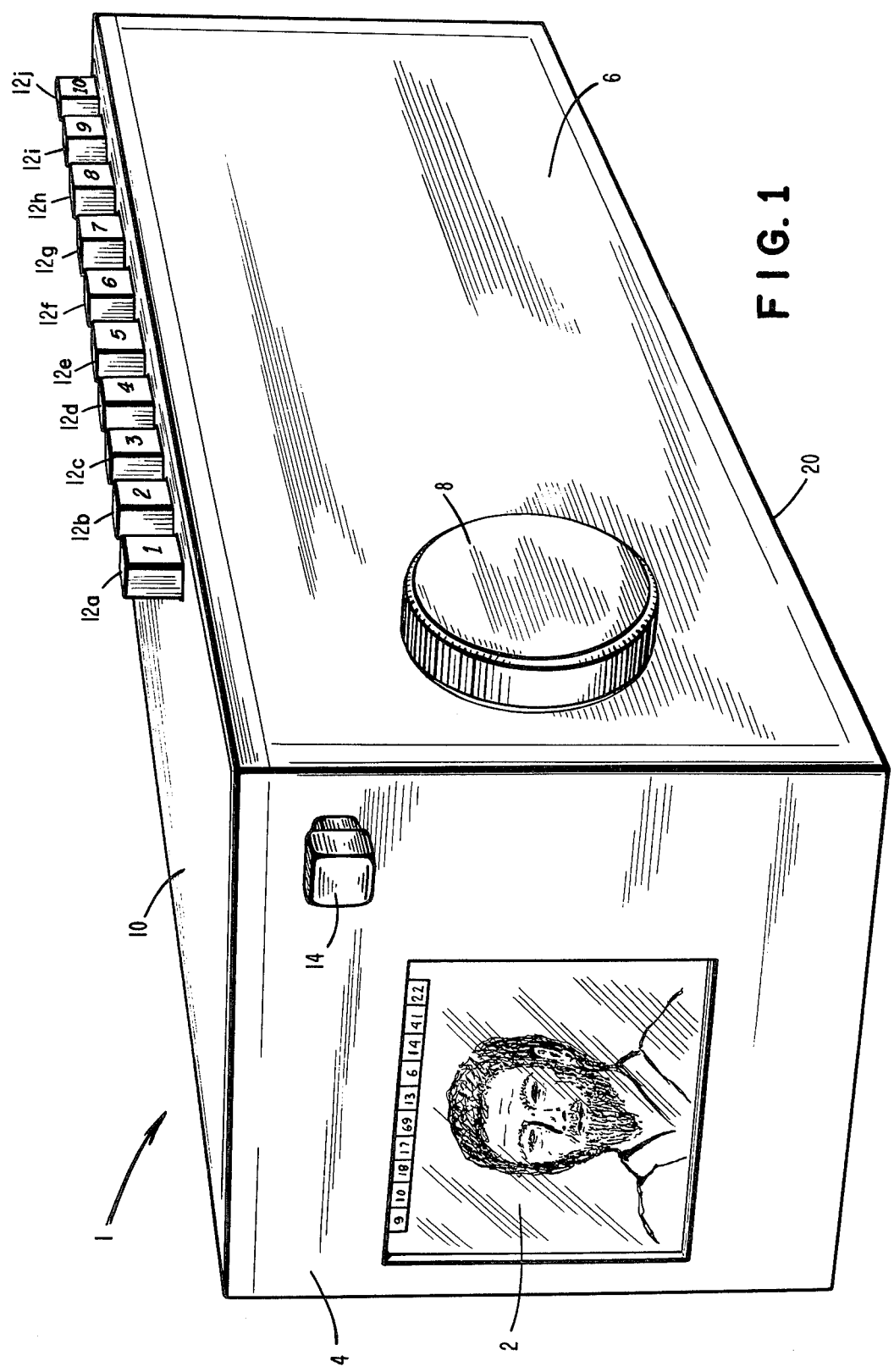
FIG. 1 illustrates a device according to one of the embodiments of the present invention.

One of the preferred embodiments utilizes a single control knob and an internal gear configuration as illustrated in FIGS. 1-7. The device 1 in FIG. 1 has an aperture 2 in the front panel 4 through which the operator views the composite image being formed within the device. The single control dial 8 extends from the right side panel 6 to control the positioning of each of the individual film strips forming the composite. The ten projecting control key caps 12a-j on top panel 10 can be individually depressed into engagement so that as the control dial 8 is turned, one of the ten films will be rotated.

The key button return slide 14 in the front panel normally functions to retain a single control key 110 in a depressed, engaged position. Pulling out knob 14 permits the spring biased depressed control key to return upward to its non-engaging position.

Figure 2:
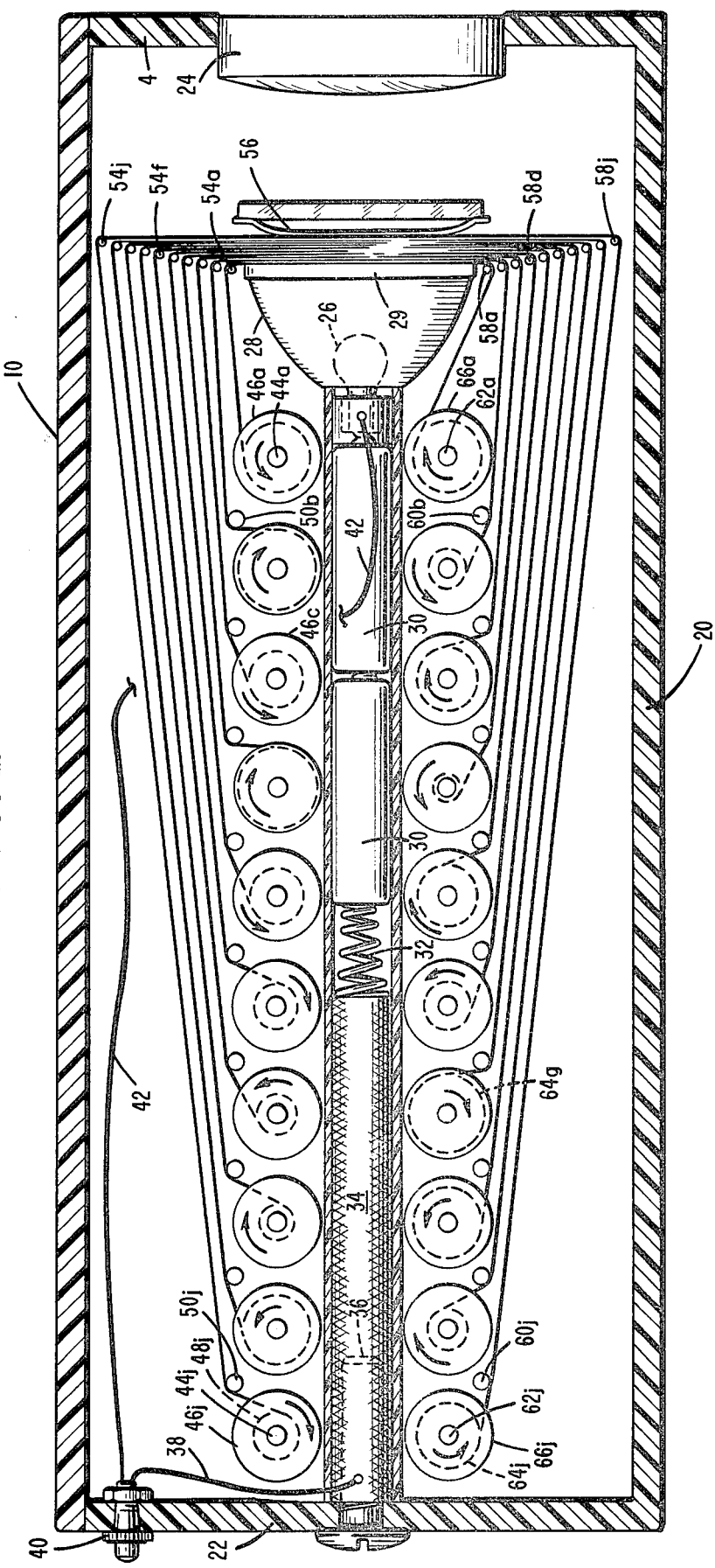
FIG. 2 is a cross-sectional side view of the device shown in FIG. 1.

A cross-sectional side view of the device through the middle is shown in FIG. 2 with bottom panel 20, back panel 22, top panel 10, and front panel 4. The magnifying lens 24 in the front panel enhances the viewing of the composite image made of the superimposed small images on each of the ten 35 mm film strips.

The composite film image is illuminated by a light bulb 26 positioned in lamp shade 28 that is connected to a lamp assembly plate behind the film. Any type of power source can be used to light the lamp, such as a 110 household voltage, a 12 volt car battery, etc., which have had their voltages appropriately reduced. In the illustrated embodiment batteries 30 positioned in the central portion of the device are employed. Battery compression spring 32 maintains the batteries in electrical contact and a conductive spacer element 34 in the battery channel provides electrical contact with the battery access screw cap 36. Electrical element 38 extends from the screw cap and spacer element to a push button switch 40 which is connected by wire 42 to the other terminal of the light.

Spaced along the length of the device are ten pairs of film reels. Although greater or lesser than ten film rolls could be used, composites made from ten films have been found to be adequate for facial identification. The device, of course, can be used with other films having different types of images. The upper reel consists of film reel spools 44a–j having spool edges 46a–j on either side. Each 35 mm film 48 is wound on its corresponding spool and passes up over its film guide roller 50a–j to the front of the device where it passes over its film position comb 54a–j. The comb can be in the form of a roller or a solid stainless steel rod. Each film continues over its comb and down across the front of the device where it is pressed against the light assembly surface 29 by film compressor spring 56. The film then passes down around its symmetric film position combs 58a–j and back to a film return guide roller 60b–j and then is wound around the reel spools 62a–j between the side elements 66 of the film spool. The film that has already been wound is shown as 64a–j.

Figure 3:
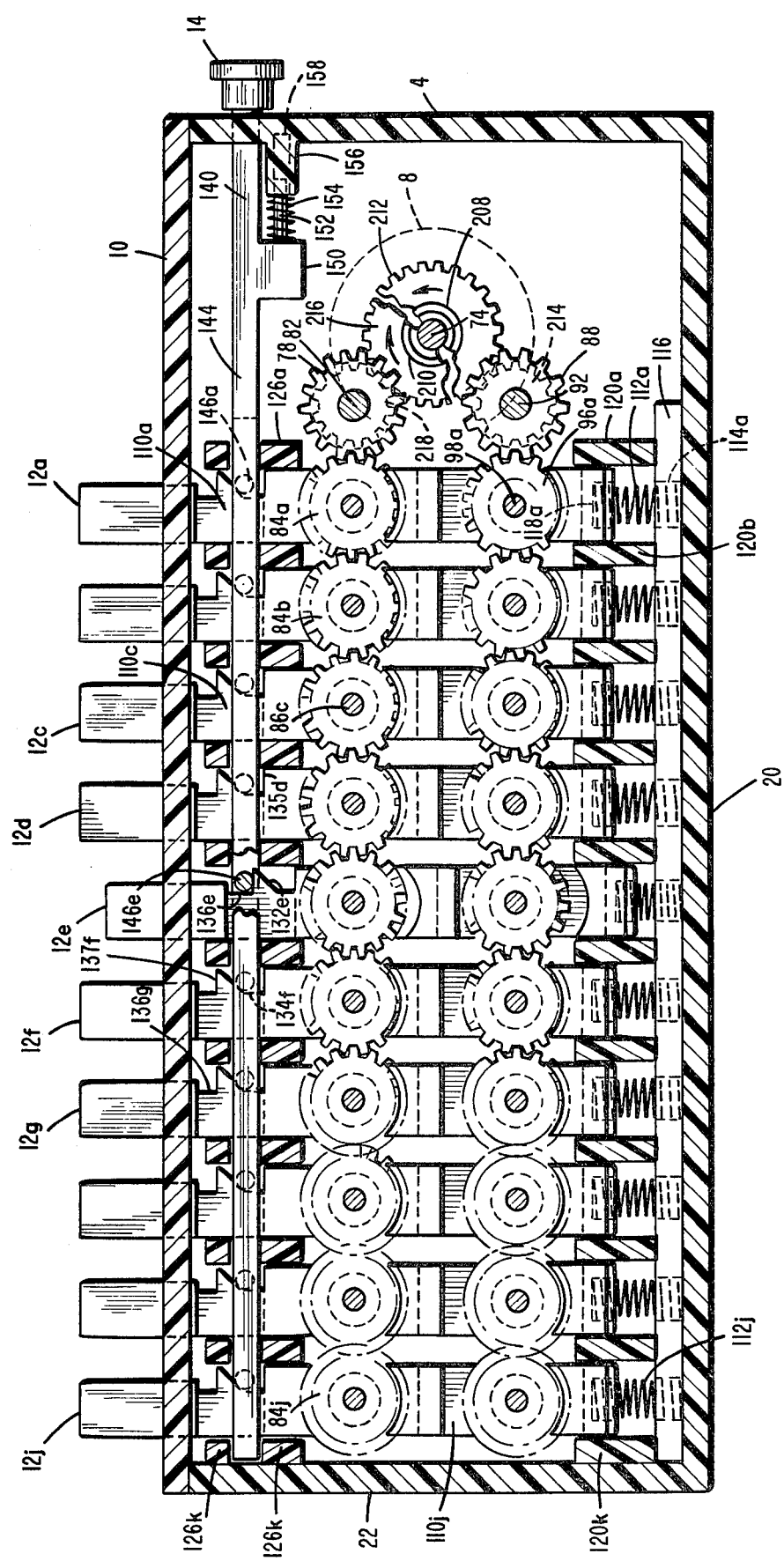
FIG. 3 is a cross-sectional side view of the device shown in FIG. 1 of the gear mechanism.

A cross-sectional view of the device through the control keys is illustrated in FIG. 3 to show the configuration of the gear train and the vertical positioning of the control keys 12. The control dial 8 rotates shaft 74 inside the device on which are two parallel independently rotating main drive gears represented generally as 212 and 216 which are seen in more detail in FIG. 5. Each of these gears is on its own one-way roller clutch manufactured by the Torrington Company, Torrington, Connecticut, which permits the shaft 74 to rotate each gear in only one direction. For a given gear, when the shaft rotates in the opposite direction, the Torrington roller clutch spins free so the gear does not rotate.

One of the main drive gears 216 engages upper gear 218 on shaft 82 and the shaft 82 in turn rotates transmission gear 78 which causes the ten gears 84a–j which are in serial engagement to simultaneously rotate about their shafts 86a–j since gear 78 engages gear 84a which in turn engages gear 84b, etc. Each of these gears 84a–j are located adjacent one of the vertically extending control keys 110. These gears are continually engaged and they all rotate as the control knob 8 is rotated in the first direction.

When the control knob is rotated in the opposite direction, the other main gear 212 is in engagement with the lower gear 214 on shaft 92. Shaft 92 in turn rotates transmission gear 88 which similarly engages a complementary series of gears 96a–j which each rotate about shafts 98a–j adjacent to the lower portion of control keys 110a–j.

As shown in FIG. 3, the control keys 110a–d and 110f–j are normally biased in an upward, nonengaging position by control key springs 112a–j with control key 110e shown down in the locked, engaged position. Each of the springs is contained within an opening 114 in the horizontal extension 116 of the right side panel 6. The other end of the spring presses against the opening 118 within the bottom of the control key 110. The vertical movement of the control key is guided by lower guide elements 120a–k which are arranged between the control keys and the upper guide elements 126a–k which also are positioned between the control key elements.

Each control key 110 in its upper section has a portion cut out of one side defined by inwardly sloping upper edge 132 extending inward to a vertical wall 134 which extends down to the inwardly extending horizontal surface 135. At the same level as this indentation defined by surfaces 132 and 135 is a key lock slide 140. As shown in FIGS. 4 and 5, the key lock slide comprises spaced apart side members 142 and 144 on either side of the control key 110 with a series of rods 146 joining the two sides. FIG. 3 shows the one side element 144 with rods 146 projecting therefrom. The slide element 140 extends the length of the device and is connected to key button return slide 14 outside of the device. In normal operation each locking rod 146 is positioned in the recessed portions of each control key defined by surfaces 132, 134, and 135.

The front end of the control key lock slide 140 has a downwardly extending member 150 with a protruding key lock slide guide rod 152 as shown in FIG. 3. This rod slides into a complementary slot 158 in projection 156 with the front panel 4. Spring 154 maintains the key lock slide guide biased in the backward direction so that the locking rods 146a–j are normally maintained against the above-described indentation in the control key.

In order to maintain a control key in a downward, engaged position, recess 136 having a horizontal surface 137 is provided in the control key at a position just above the outer edge of surface 132. By pushing down on the control key, the rod 146 will slide rightwardly against the sloping surface 132 until the surface 137 passes below the rod. At that point, spring 154 forces rod 146 into the recess 136 and maintains the surface 137 in the lowered position as illustrated by control key 110e in FIG. 3. Later when either button 14 is pulled or another control key is depressed, the rod 146e will move to the right and out of recess 136e so control key 110e will then return to its normal upward, nonengaging position due to the bias of its bottom spring 112e.

FIG. 4 illustrates a cross-sectional view when looking back from a midpoint end of the device to show the relationship between the control key and the gear driven spool. The view is taken as a section of FIG. 5. The interlocking construction of the top panel 10, the right side panel 6 with its horizontal lip 114, bottom panel 20 and left side panel 170 is illustrated. Inner panel 172 divides the device into the film area on the left and the control and gear mechanism on the right. The upper rotatable film spool support 174 extends through inner panel 172 and is connected on the right side to a spool clutch plate 178. On either side of the rotatable spool 174 are spacer extending elements 180 from the left side panel 170 and 182 from the inner panel 172. Similar construction is found in the lower part of the device where lower rotatable spool support 184 is connected through the inner panel 172 to the lower spool clutch plate 186. Again, extensions 188 from the left side panel 170 and 190 from the inner panel 172 serve as spacing elements for a film spool which fits over and engages with the lower rotatable spool support 184. In this film section the upper film guide 50 and the lower film guide 60 are as shown in FIG. 2.

When the control dial 8 is rotated in a given direction, either all the gears in the gear train in the upper section will be rotating or else all in the lower section will rotate. If, for example, a clockwise rotation of control dial 8 rotates the upper gears, then as the control dial clockwise rotates, gear 84 shown in FIG. 4, will also rotate. Since the button 12 of the control key 110 in FIG. 4 is not depressed, the rotation of gear 84 does not engage the upper rotatable spool clutch plate 178 so there is no movement of the film positioned about the upper rotatable spool support 174. The film is not subjected to any accidental movement since the spool clutch plate brake 200 positioned under the gear is in contact with the upper spool clutch plate 178 to prevent any rotation. When the control key 110 is pushed downwardly, the gear 84 and its gear shaft 86 move in a leftward direction by the beveled edge 204 of the control key to cause the gear 84 to frictionally engage the spool clutch plate 178.

A similar configuration exists in the lower section where gear 96 does not engage the lower spool clutch plate 186 since the beveled portion 206 of the lower part of the control key 110 is not yet forcing the lower gear shaft 98 in the leftward direction. Also, in this bottom section a lower spool clutch plate brake 202 is in frictional engagement with the lower spool clutch plate 186 to prevent any rotation of the lower rotatable spool support 184.

This figure also illustrates the key lock slide 140 with its right side member 142 and a left side member 144 straddling the control key 110. Between these two members is a locking rod 146.

FIG. 5 illustrates a cross-sectional perspective view of the device looking in a backward direction from the front end of the device where the main drive gears are located.

The rotation of control knob 8 rotates shaft 74 extending into the device upon which are positioned two Torrington roller clutches, each of which rotates in a single, opposite direction. Surrounding the first Torrington roller clutch 208 is the primary gear 212 which engages lower gear 214 on shaft 92. Spaced apart from lower gear 214 is a second gear 88 also connected to rotating shaft 92 which is in alignment with the remaining gears 96 in the lower train to cause them to rotate.

The second Torrington roller clutch 210 on shaft 74 rotates in the opposite direction to that of the first. Surrounding the second Torrington bearing is a primary gear 216 which engages the upper gear 218 on shaft 82. Spaced adjacent to upper gear 218 is a second gear 78 also connected to rotating shaft 82 which is in alignment with the remaining gears 84 in the upper train to cause them to rotate.

On the left film side of the device shown in FIG. 5, are the upper film position combs which are generally referred to as 230. They contain the ten combs 54a to 54j, which are maintained between the two additional side wall elements 232 and 234. Similarly, in the bottom portion referred to generally as 236, there are the lower ten film position combs 58a to 58j.

FIG. 6 illustrates an exploded view of the control key 110 and the associated upper rotatable spool support. By pressing the control key button 12, the control key 110 moves downwardly and causes the upper gear shaft 86 to move into the spool support 174 due to the increasing inward force exerted by the beveled surface 204. Shaft 86 is normally biased outwardly by spring 252 located within cavity 250 in upper rotatable spool support 174 with the shaft 86 being engaged with the beveled surface 204 of control key 110. As the upper gear shaft 86 is forced inwardly into the spool support 174, the associated gear 84 and its rubber clutch washer 192 engage the upper spool clutch plate 178 and thus rotate the spool support 174.

The upper rotatable spool support 174 shown in FIG. 6 extends through the opening 256 in the inner panel 172 and engages the bearing 254 in the side wall 170. Spacing projection element 180 extends from inner panel 170, and spacing projection element 180 extends from the side wall 170 to maintain the film spool 258 in a central position.

When the control key 110 is not in the depressed, operating position, upper spool clutch plate brake 200 engages the upper spool clutch plate 178 to prevent accidental rotation and the spool clutch plate maintains the control key within the device.

FIG. 7 is a perspective view of the control key shown in FIG. 6. The two elements 142 and 144 of the key lock slide 140 straddle the control key 110 and have the locking rods 146 extending between them. The beveled surfaces 204 and 206 on the upper and lower portions respectively of the control key engage the spring biased gear shafts. The upper spool clutch plate brake 200 with its braking surface 260 engages surface 262 of the upper spool clutch plate 178.

Figure 8:
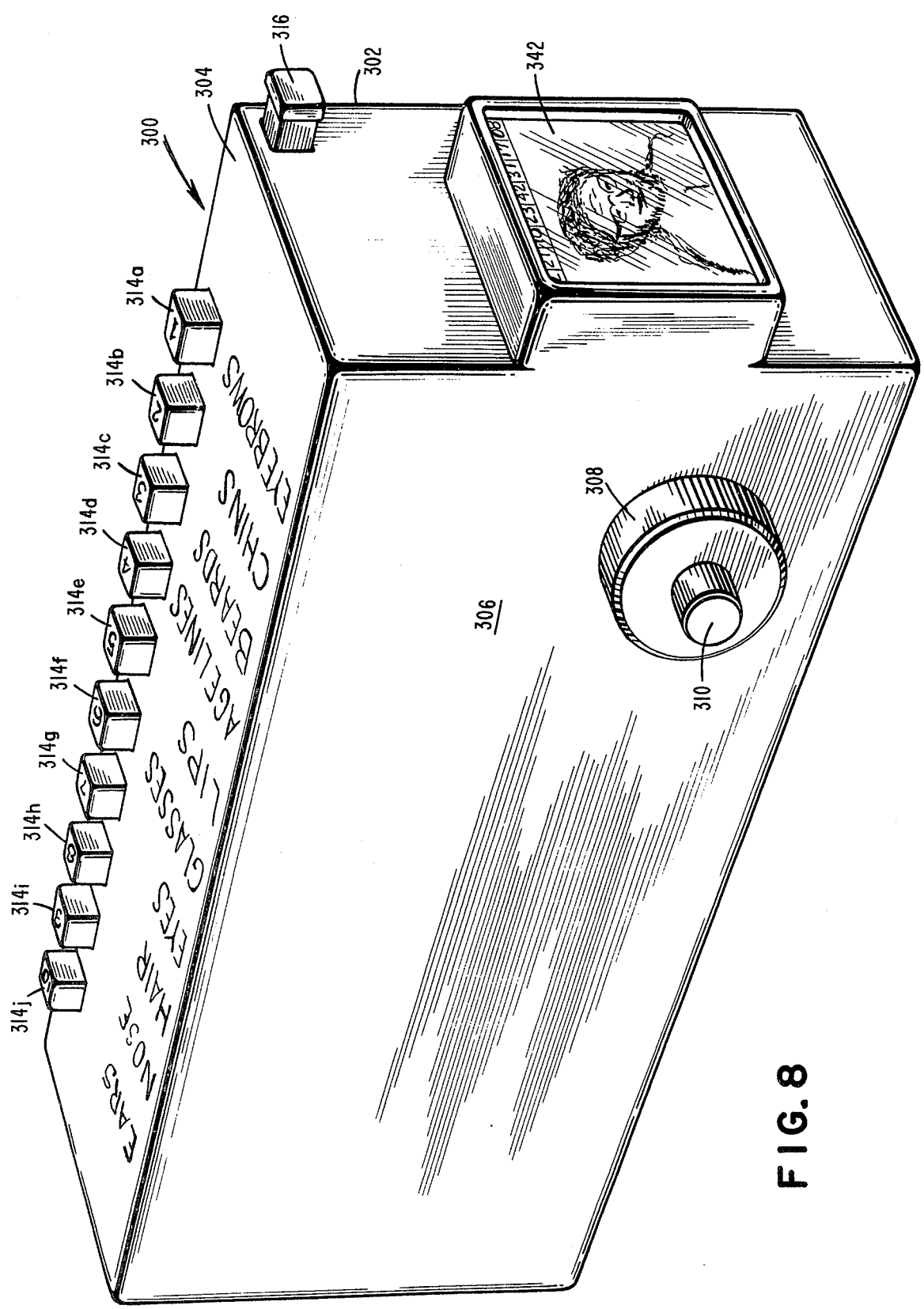
FIG. 8 illustrates a device according to a second embodiment of the invention.

A second embodiment of the viewing device without a gear train drive is illustrated in FIGS. 8–14. The external view in FIG. 8 is similar to the first embodiment illustrated in FIGS. 1–7. It consists of the unit 300 having the front panel 302, a top panel 304, a left side panel 306 through which extends control dial 308 with a small vernier control 310. Control buttons 314a–j extend through the top panel 304 and permit each of the ten film units to individually engage the drive transmitted from control dial 308. The key button return slide 316 on the front panel 302 has the same function and structure as does return slide 14 described in the first embodiment.

The cross-sectional view in FIG. 9 illustrates the drive mechanism. Here the back panel 318 and the bottom panel 320 are shown in addition to the front panel 302 and top panel 304. The drive mechanism is made of an upper O-ring 322 and a lower O-ring 324. When the external control dial 308 is rotated, its connecting shaft 325 shown in this figure rotates the two Torrington roller clutches. One of the roller clutches is within a first O-ring drive assembly 326a which engages the lower O-ring, and the second roller clutch is within the second O-ring drive assembly 326b which engages the upper O-ring as further illustrated in FIG. 11. The two Torrington roller clutches are arranged to transmit rotation in opposite directions so that as the control knob is rotated in one direction, one of the O-rings rotates while the other is disconnected and free-floating. Similarly, when the control knob rotates in the opposite direction, the reverse occurs. The O-ring compressor roller 328 maintains the two rings in contact with the O-ring drive assemblies 326a and 326b.

The lower O-ring 324 is driven by drive assembly 326a and passes over O-ring guide roller 330 to the back of the device where it passes up around a similar O-ring guide roller 334 and along a series of horizontal guide rollers 340j–a to the front of the device.

Figures 10, 11:
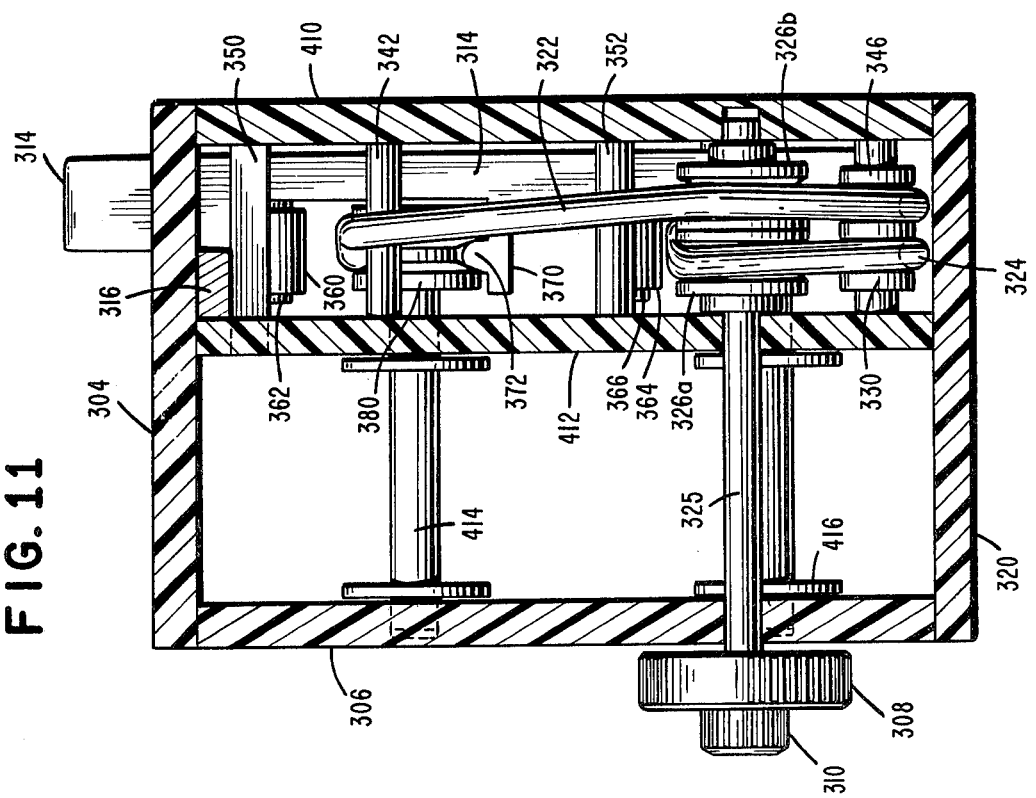
FIG. 10 is a cross-sectional end view of the device taken along the line A—A of FIG. 9.
FIG. 11 is a cross-sectional end view of the device taken along line B—B of FIG. 9.

The upper O-ring is driven by guide roller 326b and passes up over a series of horizontal guide rollers 342a–k. It passes downward to a back roller 342 (not shown) behind roller 332 and then to the front of the device where it returns up around O-ring guide roller 346 (shown in FIG. 11) to O-ring drive assembly 326b as shown in FIG. 11.

The control keys 314a-j are guided in their vertical movement by upper key slide guide studs 350a-k and at an intermediate position by a similar series of control guide studs 352a-k. As in the first embodiment, each of the control keys has a spring 354a-j to return the control key in the upright position. The springs are positioned in openings 356a-j in bottom panel 320 and extend into openings 358a-j in the bottom of the control keys.

Each of the control keys has a perpendicularly extending shaft 362a-j about which rotates a corresponding O-ring engaging roller 360a-j. Positioned below these rollers are horizontal shelf extensions 370a-j with semicircular vertically extending brake members 372a-j thereon as seen in FIGS. 10 and 12. A similar construction is found in the bottom portion of the control key for the lower O-ring. There engaging rollers 364a-j rotate about shafts 366a-j extending from the control keys. Again below these rollers are the lower horizontal shelf projections 374a-j having thereon the semicircular brake elements 376a-j as also seen in FIGS. 10 and 12.

This cross-sectional view illustrates the upper film spool pulleys 380a-j which rotate the upper film spools. These pulley and shaft assemblies are not connected to the control keys 314a-j. A similar construction is found in the lower section where the lower spool pulleys 386a-j engage the shafts 386a-j which rotate the lower film spools.

The FIG. 9 also illustrates the end of the battery holder assembly 390 with electrical element 392 connected to push button switch 394 which is in switch engagement with the return electrical element 396 connected to the light within the device.

Spring 398 retains the control key return slide element 316 in an inwardly directed position so that it is in engagement with all of the control keys 314.

FIG. 10 is a cross-sectional view taken along line A—A of FIG. 9 when looking toward the front of the device. Walls 306 and 410 support top panel 304 and bottom panel 320 with inner panel 412 dividing the device into the film section on the right and a drive section on the left. The upper spool pulley 380 is on shaft 382 which extends through opening 418 in the inner panel 412 and into the opening 422 in wall 306 which serves as a bearing for the shaft. Around the shaft in the film section is upper film spool 414.

A similar construction is found in the lower section where lower spool pulley 384 is on shaft 386 which passes through opening 420 in inner wall 412 and then into opening 424 in wall 306 which serves as a bearing for the shaft. Around the shaft in the film section is lower film spool 416. The control key 314 shown in FIG. 10 is locked in the downward engaging position with roller 360 forcing the upper O-ring 322 into engagement with the upper spool pulley 380 and roller 364 forcing the lower O-ring 324 into engagement with pulley 384. When the control dial 308 is rotated in one direction, for example, then only the Torrington roller clutch driving the upper O-ring will be rotating and thus only the upper spool pulley 380 will rotate to wind the film around film spool 414. When the control knob 308 rotates in the opposite direction, then only the lower O-ring 324 will be driven by the other Torrington roller clutch and in that case only the lower spool pulley 384 rotates to wind the film on the lower spool 416.

As also seen in FIG. 10, when the control key 314 is depressed against spring 354, the rollers 360 and 364 engage the O-rings with the spool pulleys 380 and 384 while the brakes 372 and 376 on shelf extensions 370 and 374 respectively are moved out of braking engagement with the spool pulleys 380 and 384 so that they are free to rotate.

FIG. 11 presents the view taken along section line B—B in FIG. 9 when looking from the front of the device as shown in FIG. 9 toward the back of the device.

This view shows the relationship between the control dial 308 with its associated shaft 325 and the O-ring drive assemblies 326a and 326b. Each of these pulleys 326a and 326b are engaged about a separate Torrington one-way roller clutch on shaft 325 with each roller clutch transmitting rotation in an opposite direction. As a result, when the control knob 308 is rotated in one direction, only one of the pulleys 326a or 326b will rotate; and when the control knob 308 is rotated in the opposite direction, the other pulley will rotate. When a pulley is not being rotated by the control dial 308 and its associated shaft 325, then the pulley is in a freewheeling condition, and it will rotate only if its associated O-ring is moving.

In FIG. 11 the control key 314 is shown in the upper, locked position. Here the brake 372 on shelf extension 370 engages in a braking relation with the upper spool pulley 380 to prevent any rotation of the pulley spool 380 and its associated film spool 414.

FIG. 12 illustrates a perspective view of the control key 314 with its engaging rollers 360 and 364 which rotate upon fixed shafts 362 and 366. Associated beneath each of these rollers are the horizontal shelf projections 370 and 374 upon which braking elements 372 and 376 are located to engage in a braking relation with the spool pulleys 380 and 384.

FIG. 13 illustrates a schematic arrangement in which the control key return slide 316 has triangular elements which extend between the two sides of the slide assembly to engage the inwardly beveled portion of the control key 314 in a manner similar to the round rods 146 shown in FIG. 7 of the first embodiment.

A third embodiment of the invention is a multi-roll film viewer with individual control knobs as shown in FIGS. 14-24.

Figure 14:
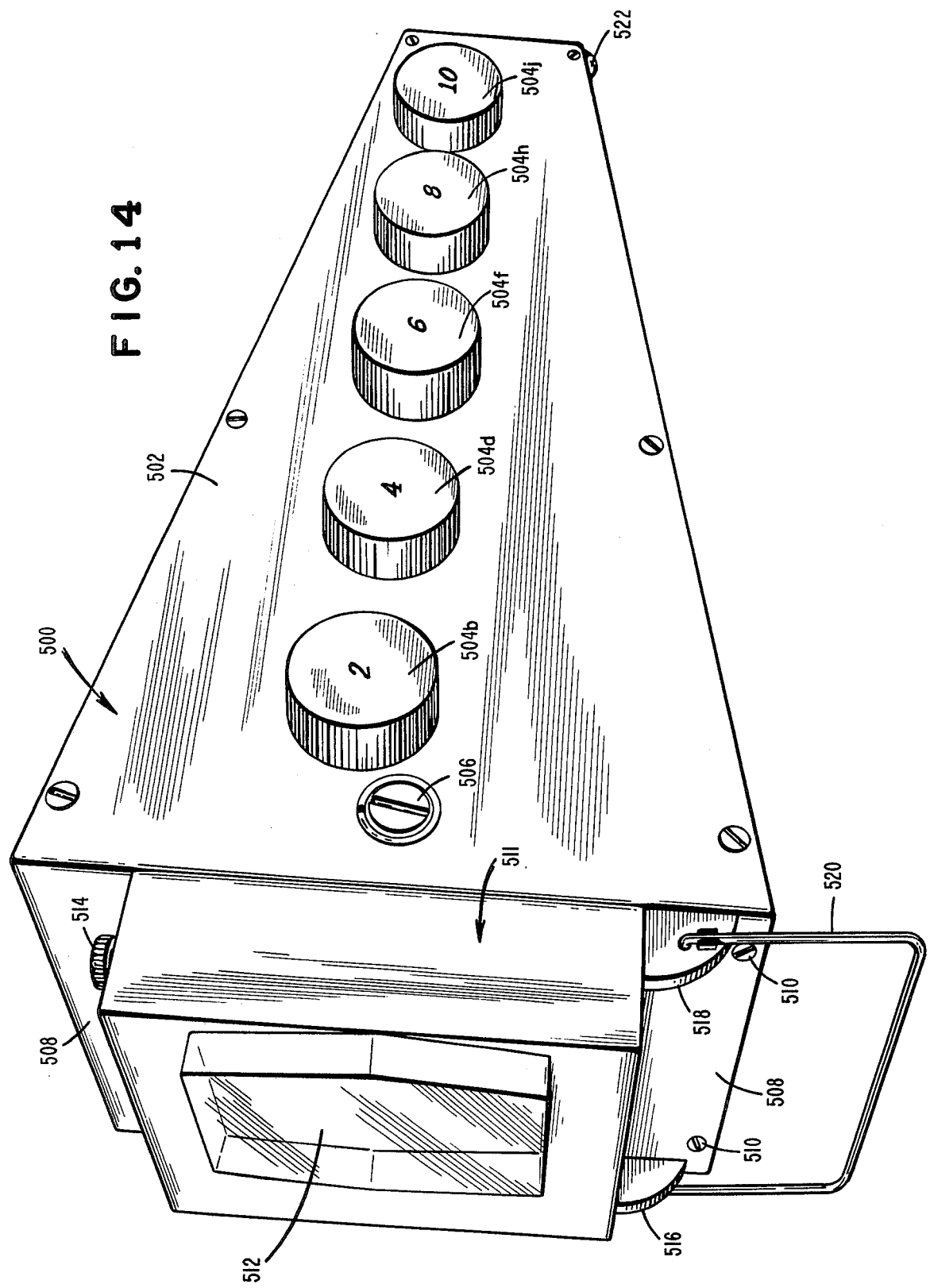
FIG. 14 illustrates a device according to a further embodiment of the present invention.

In FIG. 14 the device is generally shown as unit 500 having one side 502 with a series of hand-controlled film rollers 504b, 504d, 504f, 504h, and 504j. These five rollers on this side control five of the film rollers while on the opposite side there are an additional five rollers to rotate the remaining film rollers. A lamp access screw plate assembly 506 in the side wall 502 can be opened to change the lamp. Extending from the front wall 508 is a viewing assembly 511 with an opening 512 in which is placed a four power viewing lens to magnify the composite film image on, and an on-off push button switch 514 on top of the assembly 511 turns on the light behind the film to illuminate this composite image. Support elements 516 and 518 below the viewing extension hold a swivel wire stand 520 which can be rotated down to the position shown in FIG. 14 to elevate the front end of the device. At the back end a rubber bumper 522 prevents the device from slipping when placed on a flat surface.

Figure 15:
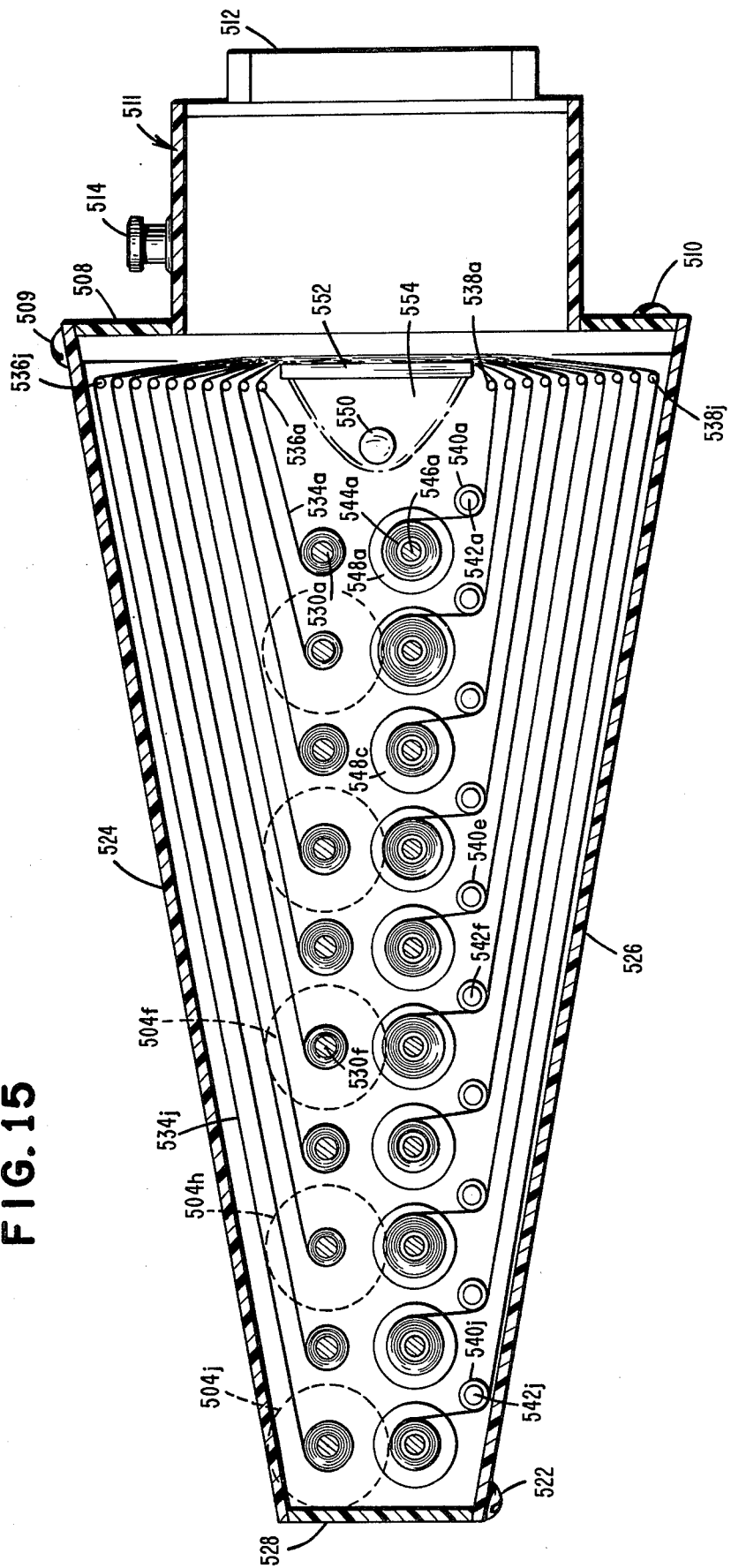
FIG. 15 is a cross-sectional side view of the device as shown in FIG. 14.

FIG. 15 illustrates a side view from the side opposite the one shown in FIG. 14 with top and bottom walls 524 and 526, and back end wall 528. The viewing assembly 511 projects from front wall 508 and has the lens 512 and on-off switch 514. Positioned within the device are ten film assemblies. They each contain upper film rollers 530a–j onto which the film ends can be taped to the shafts. The films 534a–j from the rollers 530a–j extend over upper film rollers 356a–j and down past the viewing screen to lower rollers 538a–j where the films then pass over lower film roller guides 540a–j which rotate about shafts 542a–j. The films are then wound onto rollers 544a–j which rotate about shafts 546a–j. Rollers 544a–j have side elements 548a–j to guide the film.

In the gear train to be described below, there can be slip and play when the lower gear is driven by indirect drive. To overcome this effect the diameter of the lower roller is selected to have a larger diameter than the upper roller or shaft. The difference in diameters can be varied with the lower roller preferably being about 30% larger than the effective diameter of the upper roller. Spacer elements can be placed on either side of film roller shaft 530a–j and film roller 544a–j to align the film when the length of the shafts in the film section is greater than the width of the film.

Around lamp 550 is a lamp shade 554 to direct the light to the viewing surface plate 552 upon which the composite film images are pressed. The lens 512 can be a four power lens with a focal length of three inches which is the approximate distance between the lens and plate 552 upon which the composite film image is formed.

Figure 16:
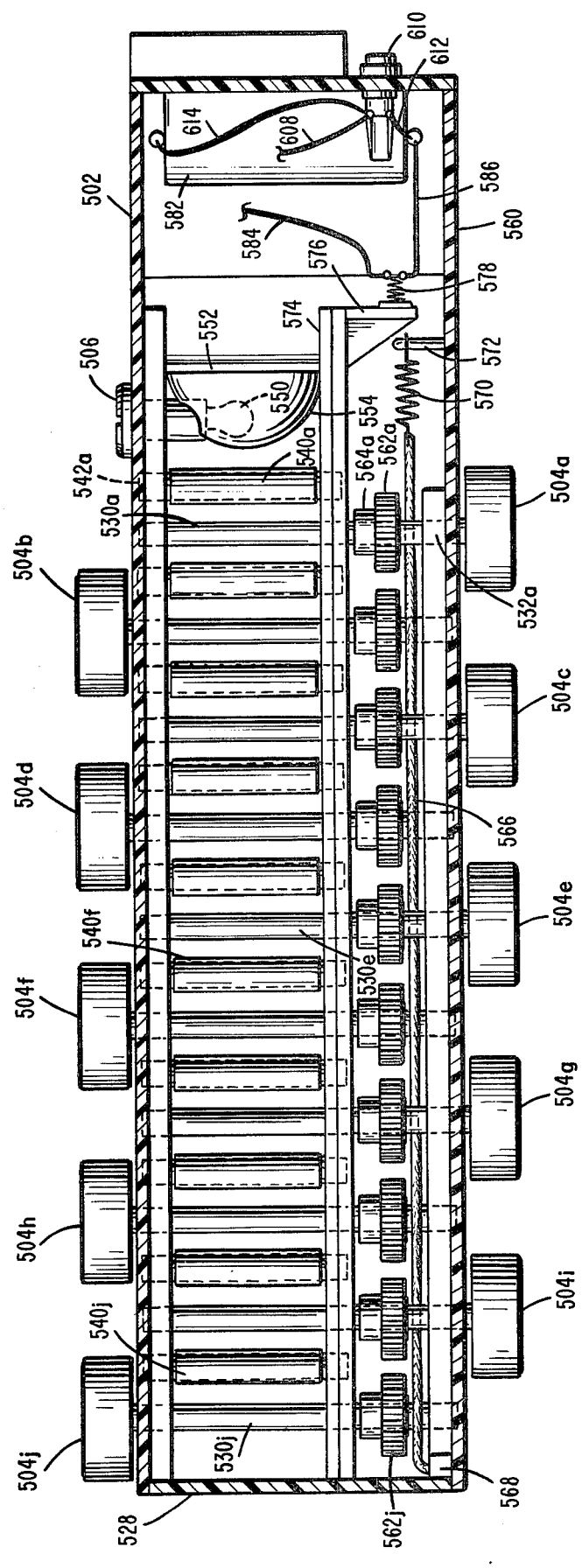
FIG. 16 is a cross-sectional top view of the device shown in FIG. 14.

FIG. 16 presents a top view showing the relationship of the five control dials on each side of the device. Extending from wall 502 are the control dials 504b, d, f, h, and j while from the opposite wall 560 extend control dials 504a, c, e, g, and i. Each of these control dials directly rotates the upper film roller shafts 530a–j to which one end of the film is attached.

Figure 17:
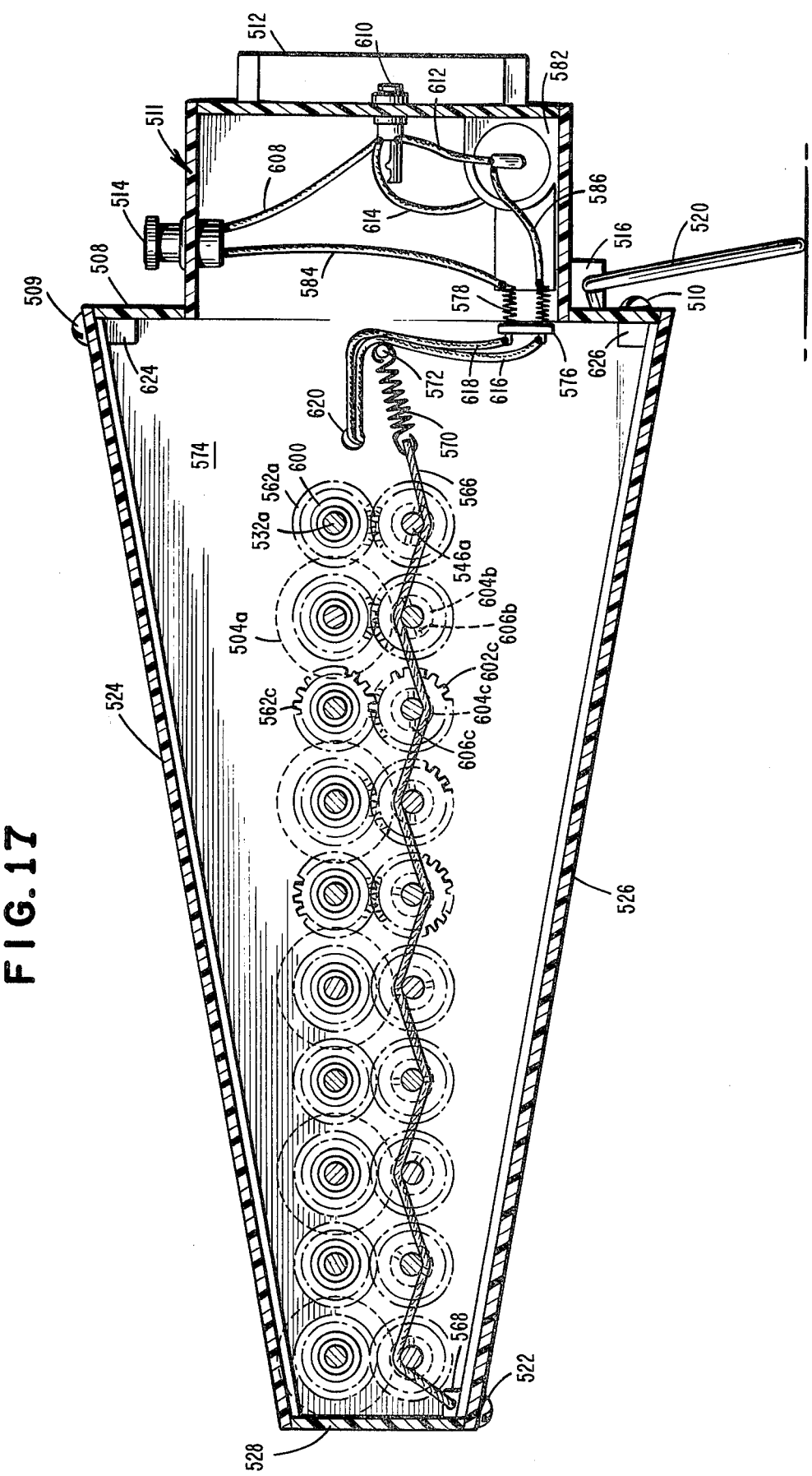
FIG. 17 is a cross-sectional side view of the device shown in FIG. 14 illustrating the gears.

Attached to each of the shafts is part of the one-way drive mechanism which includes Torrington one-way roller clutches 600a–j as shown in FIG. 17 over which are fitted gears 562a–j. The Torrington roller clutches allow the gears to rotate with the shaft when the control knob is turned in a first direction. However, when the control knob is turned in the opposite direction, the Torrington roller clutch does not transmit the rotation of the shaft to its outer surface so the surrounding gears 562a–j do not rotate and consequently, do not rotate the lower gears 602a–j as shown in FIG. 17.

FIG. 17 illustrates a side view of the device taken along a vertical plane through the gears. As in FIG. 15, the top wall 524, bottom wall 526, and end wall 528 are shown with the upper and lower rows of rotating shafts. The upper row comprises shafts 532a–j around which are the Torrington roller clutches 600a–j surrounded by upper gears 562a–j. These upper gears 562a–j engage the lower gears 602a–j on lower shafts 546a–j. Each of the lower gears has a projection 604 extending from the gear which is divided into two sections by the slit 606 as shown in FIGS. 18, 22, and 23. Compression spring 654 around this projection serves as an adjustable driving engagement element and is adjusted in compression to permit the gear to rotatably engage the shaft while further permitting the gear to slip about the shaft when necessary. For example, when the lower roller is being indirectly driven to wind the film on it, the gear will slip on the shaft since the lower roller has a larger diameter than the upper roller.

The drag line 566 shown in FIGS. 16, 17, and 19 is anchored at the back end by anchor 568 and is held in tension by spring 750 that engages anchor 572 at the front end of the device. The drag line is threaded under and over the successive lower shafts 546a–j on the surface of the shaft between the gears 602a–j and the wall 560 to allow the Torrington clutch to index while backstopping. The play between the engaging upper and lower gears would not allow the Torrington roller clutch to index properly and keep proper tension on the film. Thus, the drag line serves as a drag means to keep the gear teeth in a non-play mesh engagement.

The electrical power supplied in the front portion 511 of the device is transmitted by means of electrical springs 578 to a stationary contact power plate 576 in the other portion of the device which in turn is connected to lines 616 and 618 that pass through hole 620 in the inner panel 574 to the light 550. One of the springs is connected by line 586 to one end of the battery 582 while the wire 584 connected to the other spring engages the on-off switch 514. The other terminal of the on-off switch is connected by wire 608 to an external jack 610 which in turn is connected in parallel with the battery 582 by wires 612 and 614.

The external jack 610 permits the use of power which can be supplied by either an adaptor which converts 110 volts to 3 volts or by an adaptor such as one which fits into a lighter of an automobile to convert 12 volts to 3 volts as further shown in FIG. 18.

As shown in FIG. 17, front sections 508 and 511 attaches to the rest of the device by screws 509 and 510. Screw 509 passes through top 524 and screws into stud 624 which is integral with the front wall 508. Similarly, screw 510 passes through front wall 508 and screws into lower stud 626 which is integral with the bottom wall 526.

FIG. 18 illustrates schematically the electrical wiring for the device. Battery 582 is connected in parallel with the external jack 610 and these two power sources are connected to lamp 550 via the push button switch 514. The external jack 610 can be supplied with external power either by means of a 12 volt source with an adaptor to reduce it down to 3 volts or by means of a 110 volt source which also has an adaptor to reduce it to 3 volts.

FIG. 19 is a detailed view of the upper and lower shafts with their gears in engagement. In the upper portion of the figure, control knob 504 rotates shaft 532 upon which is a Torrington roller clutch with gear 562 surrounding the clutch. Shaft 532 is supported by the three walls and passes through opening 642 in wall 502 and opening 644 in middle wall 574 and terminates in bearing 646 in wall 560. The rotation of shaft 532 in one direction is transmitted by the Torrington roller clutch and gear 562 to the lower gear 602 which in turn rotates shaft 546. Shaft 546 is positioned within bearing 648 in wall 560, passes through opening 650 in middle wall 574, and terminates in bearing 652 in wall 502. To maintain the gear 602 in slip engagement with the shaft, compression spring 654 compresses together the two portions of the gear extension 604.

The engagement of the two gears is shown in further detail in FIG. 21 and the lower gear 602 is shown in further detail in FIGS. 22–24.

FIG. 19 illustrates the drag line 566 which is in frictional engagement with the bottom shaft 546. Also illustrated is the lower guide roller 540 which rotates about shaft 542 that is positioned within bearing 658 in wall 574 and bearing 660 in wall 502.

FIG. 20 is a detailed section looking through opening 512 to show the construction of the upper and lower comb guides 536 and 538. The outer wall 502 is made of a thin section 502a and a second section 502b with bores to hold the shafts about which rollers 536a-j and 538a-j rotate. Similarly, the middle wall 574 has a first portion 574a and the second portion 574b in which similar bores hold the opposite ends of the shafts for rotating rollers 536a-j and 538a-j. Film alignment guide plates 670 and 672 are positioned adjacent inside walls 502 and 574 to guide and align the film as it passes through the viewing section. Rectangular box 674 presents a reference mark to align the identifying indicia on each of the films to make the images congruent.

FIG. 21 is a detailed view of the engagement of the two gears with the upper gear 562 surrounding a Torrington roller clutch 600 which engages the rotating shaft 532. The upper gear 562 is in gear engagement with the lower gear 602 which engages lower shaft 546 due to the pressure that compression spring 654 exerts on the two halves of the gear extension 604 to cause them to frictionally engage the shaft 546.

FIGS. 22 and 23 are detailed end and side views of the lower gear 602 showing the extension 604 which is divided into two sections by the slit opening 606.

FIG. 24 illustrates three possible positions for the compression spring 654 to be oriented about the extension 604 with respect to the slit opening 606. In position I the maximum compression of the spring is obtained since the spring is forcing the two sections together across the slit opening 606. By positioning the ends of the compression spring 654 at position II, the two sides of the compression ring do not exert such a large force on the two halves of the gear extension 604 against the shaft 546, and a position III the least pressure is exerted.

Figure 25:
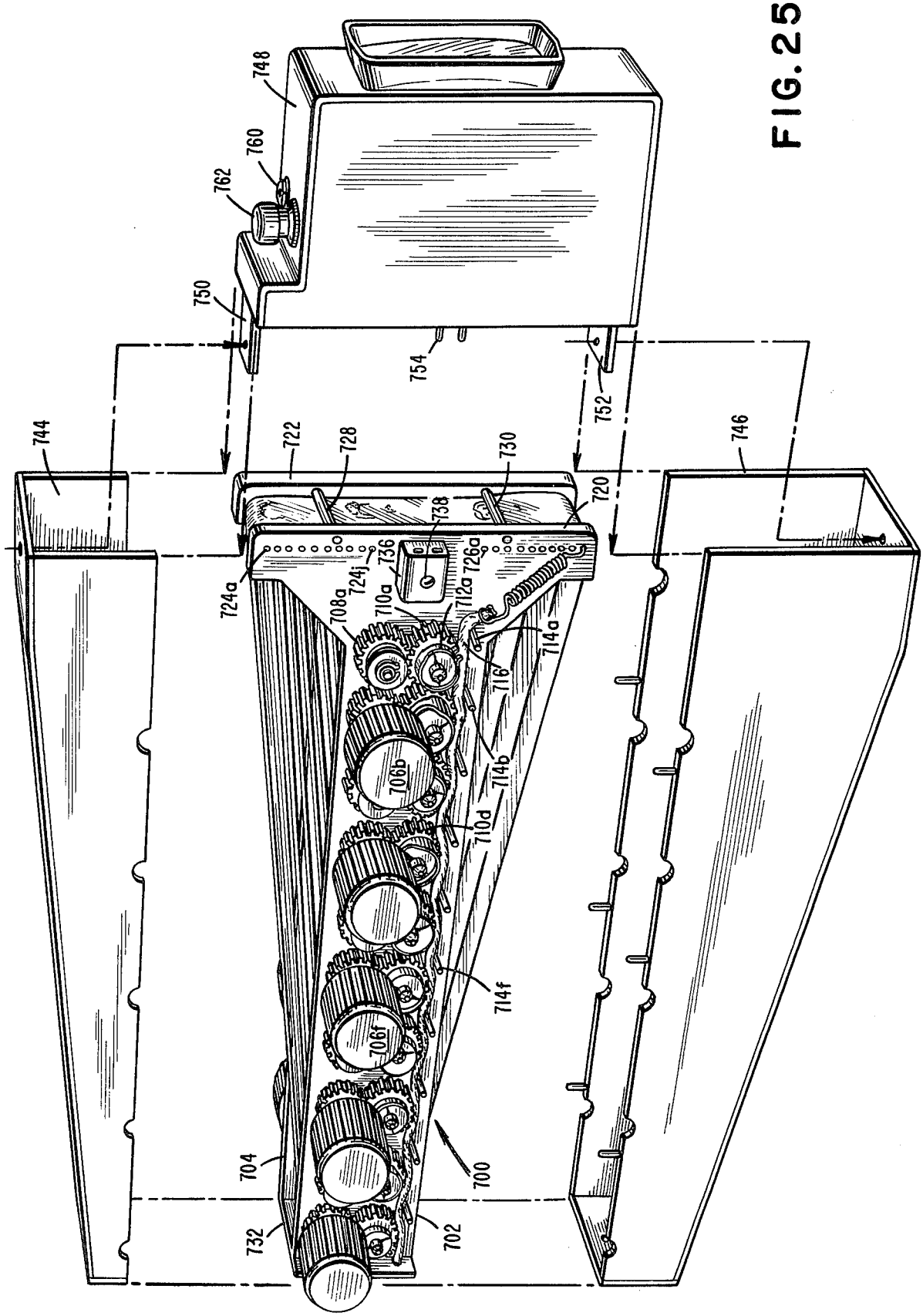
FIG. 25 is an exploded perspective view of a device according to a further embodiment of the present invention.

The multi-control knob embodiment shown in FIGS. 14-24 can be further modified to have all of the film spool rollers and the associated controls on a single, internal frame element which can be easily assembled inside the top and bottom cover members. FIG. 25 is an exploded perspective view of this embodiment. The center portion is the integral frame unit generally designated 700 made of the two longitudinal walls 702 and 704 between which are spaced the ten upper film control elements 706a-j which are made of the control knobs on alternate sides as shown in FIG. 14, and the gears 708a-j which are on Torrington roller clutches and which are located outside of the wall 702. These upper gears engage the lower gears 710a-j in a manner shown in FIG. 19. The upper and lower shafts are supported by the walls 702 and 704 and the compression springs 712a-j are positioned on the gears which are outside of wall 702 as shown in FIG. 25. The lower film guide rollers are on shaft pins 714a-j which extend from wall 702 underneath the lower gears and between these pins and the lower gears is a drag line 716 preferably made of nylon rope that allows the Torrington roller clutch to index while backstopping as discussed with regard to the corresponding function of the drag line 566 in FIGS. 17 and 19.

As in the previous embodiment, the diameter of the lower, indirectly driven roller is larger than that of the upper film winding element and the lower gears 710a-j are adapted to slip on the lower shafts 714a-j.

The front end of the internal frame unit 700 has vertically extending members 720 and 722. In the upper portion there are ten film comb rollers 724a-j which can be steel rods with plastic cylindrical rollers rotating about the rod. In the lower portion there are the similar ten lower rollers 726a-j.

On the front edge of the two vertical walls 720 and 722 are two additional rollers 728 and 730. The ten films are threaded inside these rollers so that two rollers serve as aligning means to compress the ten films together in the central viewing section.

The rigidity of the two walls 702 and 704 of the internal structure is maintained by the connecting back wall 732.

Power receiving plug 736 attaches to side wall 702 and front vertical wall 720 by screw 738 which extends into wall 720. By removing the screw 738, the plug 736 and its associated light socket and light bulb are removed to permit replacement of the light bulb. After the bulb has been replaced, the plug 736 is screwed back into the wall 720 so the light bulb extends behind the composite films inside the light reflecting shield.

As shown in exploded view 25, the upper cover member 744 and lower cover member 746 fit around this integral central unit and are secured by screws into the back wall 732. The front end of the device has a power supply and viewing member 748 which generally corresponds to the viewing assembly 511 in FIG. 15. In this embodiment the bottom wall is made flush with the bottom of the lower cover member 746 with a lens positioned within the assembly to magnify the composite image. The viewing assembly 748 has support extensions 750 and 752 which extend back from the top and bottom underneath the upper cover member 744 and above the lower cover member 746 respectively. The front end view assembly is fastened to the rest of the device by sliding these two support extensions within the top and bottom covers and screwing them together. Also extending back from the viewing assembly 748 is plug 754 which makes the electrical connection with plug 736 to transmit the power supply in the front of the device to the light behind the composite film strips.

As shown in FIG. 25, the external power receiving jack 760 may be located on top of the front viewing assembly adjacent to the on-off push button switch 762.

What is claimed is:

1. A viewing device for illuminating and positioning a plurality of superimposed film images comprising
a housing having at one end a viewing lens,
a light source within said housing spaced from said viewing lens,
a plurality of spaced roller pairs positioned about said light source, comprising a series of first rollers and a corresponding series of oppositely spaced second rollers,
a plurality of indicia-bearing roll films each film being secured at one end to a roller of said roller pairs,
guide means to direct each film from one of said first rollers past said light source and onto a corresponding second roller of said roller pair,
means to maintain said plurality of films between said viewing lens and said light source is approximately the same focal plane, and
film positioning control means for winding each of said films independently back and forth between its respective pair of spaced rollers without binding the film comprising
only one rotatably external control knob,
an associated internal drive means driven by said external control knob, and only one external engaging element for each roller pair to engage both rollers of the roller pair with said drive means.

2. A viewing device according to claim 1, wherein said external engaging element of said film positioning control means comprises an engaging means for each roller pair normally locking each roller pair and capable of engaging said roller pair with said driving means whereby each indicia-bearing roll of film can be individually positioned in the focal plane of said viewing lens to produce a composite image.

3. A viewing device according to claim 2, wherein said rotatable external control knob and said internal drive means comprises a single control rotatable element on the outside of said housing, two primary gears mounted on oppositely rotating external one-way clutches inside said housing, a rotatable shaft connecting said outside control rotatable element and said two primary gears, a first gear train connected to one of said primary gears with each engaging gear capable of rotating a first set of rollers in said roller pairs, and a second gear train connected to the other of said primary gears having each engaging gear capable of rotating the second set of rollers in said roller pairs whereby when said control rotatable element is rotated in one direction, only one of said primary gears and its associated gear train rotate while the other primary gear and its associated gear train are free of driven rotation.

4. A viewing device according to claim 3, wherein said engaging means for each roller pair comprises a movable control key adapted for longitudinal movement along its length and a pair of roller holder assemblies spaced from said key in longitudinal alignment, said roller holder assemblies comprising a hollow shaft mounted for rotation with the end facing said control key having a flange clutch plate and with a film spool engaging the outside of said hollow shaft positioned between said flange and the inner wall of said housing, said control key having two inwardly beveled portions along its length spaced from said two roller holder assemblies, two axially movable gear alignment shafts slidingly positioned within each hollow shaft and each in spring bias engagement with a beveled portion of said control key, a gear on each gear alignment shaft with an annular edge clutch face adapted to engage said flange clutch plate, the two gears of each roller pair engaging element being in engagement with the similar gears of the roller pair engaging elements on either adjacent side, two flange clutch plate braking means extending from each control key to normally lock and prevent rotation of each of said hollow shafts and their accompanying spools, and control key positioning means to maintain said flange clutch plate braking means either in normal braking engagement with said flange clutch plate or to maintain said control key in an engaging position whereby said flange clutch plate braking means disengages from said flange clutch plate and said beveled portion of said control key causes said gear alignment shaft and accompanying gear to axially move into engagement with said flange clutch plate so that movement of said rotatable external control knob and said internal drive means rotates one of the spools of said roller pair.

5. A viewing device according to claim 2, wherein said rotatable external control knob and said internal drive means comprises a single control rotatable element on the outside of said housing, two primary pulleys mounted on oppositely rotating one-way clutches inside said housing, a rotatable shaft connecting said outside control rotatable element and said two primary pulleys, a first drive belt connected to one of said primary pulleys and extending adjacent to each first roller of said roller pair, and a second drive belt connected to the other of said primary pulleys and extending adjacent to each second member of said roller pairs whereby when said control rotatable element is rotated in one direction, only one of said primary pulleys and its associated drive belt rotates while the other primary pulley and its associated drive belt are free of driven rotation.

6. A viewing device according to claim 5, wherein said engaging means for each roller pair comprises a movable control key adapted for longitudinal movement along its length and a pair of roller holder assemblies spaced from said key in longitudinal alignment, said roller holder assemblies comprising a rotatable shaft mounted for rotation with the end facing said control key having a pulley thereon and with a film spool engaging the outside of said shaft positioned between said pulley and the inner wall of said housing, two drive belt rollers each extending from said control key and positioned adjacent said pulleys, two pulley braking means extending from said control key to normally lock and prevent rotation of each of said pulleys and their accompanying spools, and control key positioning means to maintain said pulley braking means either in normal braking engagement with said pulley or to maintain said control key in an engaging position whereby said pulley braking means disengages from said pulley and said drive belt roller of said control key causes each belt to engage with the pulley so that movement of said rotatable external control knob and said internal drive means rotates one of the spools of said roller pair.

7. A viewing device for illuminating and positioning a plurality of superimposed film images comprising a housing having at one end a viewing lens, a light source within said housing spaced from said viewing lens, a plurality of spaced roller pairs positioned about said light source, comprising a series of first rollers and a corresponding series of oppositely spaced second rollers, a plurality of indicia-bearing roll films, each film being secured at one end to a roller of said roller pairs, guide means to direct each film from one of said first rollers past said light source and onto a corresponding second roller of said roller pair, means to maintain said plurality of films between said viewing lens and said light source in approximately the same focal plane, and film positioning control means for winding each of said films independently back and forth between its respective pair of spaced rollers without binding the film comprising for each pair of spaced roller pairs a one-way drive means driven by an external control knob for each roller pair, said drive means compensating for the varying diameter of the two rollers as the film is rolled so that the film is wound throughout its length onto either roller without binding.

8. A viewing device according to claim 7, wherein said one-way drive means comprises a one-way drive mechanism, a first rotatable shaft serving as one of the rollers of the pair driving said one-way drive mechanism, said shaft extending outside of said housing with said external control knob thereon, a second rotatable shaft for the other roller of said roller pair, said second shaft being spaced from and parallel to the first shaft, said roller on said second rotatable shaft having a larger diameter than the effective film winding diameter of the first rotatable shaft, a gear mounted on said second shaft and driven by said one-way drive mechanism, adjustable driving engagement means to engage said gear mounted on said second shaft with said second shaft, and drag means to engage said second shafts to reduce the play in the rotation of said second shafts and to allow said one-way drive mechanism to index properly.

9. A viewing device according to claim 8, wherein said one-way drive mechanism comprises a one-way roller clutch mounted on said first shaft with a first gear surrounding said roller clutch engaging said gear mounted on said second shaft, and said adjustable driving engagement means comprising a split ring extension of said gear mounted on said second shaft with an adjustable spring clip thereon to vary the frictional engagement of said split ring to said second shaft.

10. A viewing device according to claim 8, wherein said housing comprises an internal frame made of two parallel, generally T-shaped wall members with the roller pairs extending between said two walls in the longitudinally orientated base section of the T and individual film guide elements extending between said two walls in each end of the cross section of the T, and a casing for said internal frame with an opening for said viewing lens spaced from said superimposed film images.

11. A viewing device according to claim 10, wherein said film guide elements are pins.

12. A viewing device according to claim 10, wherein said film guide elements are shafts with rollers rotatable thereon.

13. A viewing device according to claim 10, further comprising aligning means to maintain the films in approximately the same focal plane.

14. A viewing device according to claim 13, wherein said aligning means comprises two additional pressure rollers extending between the cross section of the T-shaped wall members on either side of the opening for said viewing lens, said rollers being spaced apart from said film guide elements whereby they exert pressure on said films to maintain them in approximately the same focal plane.

15. A viewing device according to claim 9, wherein said housing comprises an internal frame made of two parallel, generally T-shaped wall members with the roller pairs extending between said two walls in the longitudinally orientated base section of the T and individual film guide elements extending between said two walls in each end of the cross section of the T, and a casing for said internal frame with an opening for said viewing lens spaced from said superimposed film images.

16. A viewing device according to claim 15, wherein said first and second shafts extend externally from one of said walls of said internal frame with said first and second gears mounted on the external portion of said shafts and further comprising support elements spaced adjacent the gears mounted on the second shafts, a drag line positioned between said gears mounted on said second shafts and said support elements, and means to adjust the tension on said drag line whereby the play in said gears mounted on said second shafts is reduced allowing the one-way clutches mounted on the first shafts to index properly.

17. A viewing device according to claim 8, wherein said light source is positioned behind the composite film image between said two longitudinally orientated walls of said internal frame between said roller pairs and said viewing lens.

18. A viewing device according to claim 10, wherein said housing further comprises a front section having means to supply electrical power to said device, an on-off switch for said light source, said viewing lens mounted in said front section, and electrical connection means to transmit said electrical power to said internal frame where said light source is positioned.

19. A viewing device according to claim 18, wherein said means to supply electrical power comprises a battery within said front section and an external jack adapted to receive external power.

20. A viewing device according to claim 7, wherein there are ten films each illustrating different eyebrows, chins, age lines, beards, lips, eye glasses, eyes, hair, noses, and ears.

21. A viewing device according to claim 8, wherein said rollers on said second rotatable shafts have a diameter about 30% greater than the effective film winding diameter of said first rotatable shafts.

22. A method to illuminate and align a plurality of superimposed film images to form a composite image comprising positioning a plurality of spaced roller pairs comprising a series of first rollers and a corresponding series of oppositely spaced second rollers in a housing having a viewing lens at one end, passing indicia-bearing roll films which are secured at one end to the first roller of each spaced roller pair over a composite image forming area and then to the second roller of said spaced roller pair where the opposite end of each film is secured to said second roller, providing a light source between the films in the composite image area and said viewing lens, maintaining the plurality of films in the composite image area between said viewing lens and said light source in approximately the same focal plane, providing a single external control knob, providing a one-way drive means adapted to permit the individual rotation of each one of said series of first rollers when said control knob is rotated in a first direction while the corresponding second roller is in free rotation and adapted to permit the individual rotation of each of said second series of rollers when said control knob is rotated in the opposite direction while the corresponding second roller is in free rotation, engaging simultaneously each spaced roller pair individually with said one-way drive means; and rotating said external control knob back and forth so as to continuously align in either direction the desired film image on that roll in said composite image area whereby the film is wound throughout its length onto either roller without binding.

23. A method to illuminate and align a plurality of superimpose film images to form a composite image comprising positioning a plurality of spaced roller pairs comprising a series of first rollers and a corresponding series of oppositely spaced second rollers in a housing having a viewing lens at one end, passing indicia-bearing roll films which are secured at one end to the first roller of each spaced roller pair over to a composite image forming area and then to the second roller of said spaced roller pair where the opposite end of each film is secured to said second roller, providing a light source between the films in the composite image area and said viewing lens, maintaining the plurality of films in the composite image area between said viewing lens and said light source in approximately the same focal plane, providing a series of external control knobs each engaging a separate one-way drive means for each roller pair, said one-way drive means providing compensation for the varying diameter of the two rollers as the film is rolled, and aligning the indicia on each film to the desired position in the composite image area solely by rotating each external control knob back and forth so as to continuously move the film in either direction whereby the film is wound throughout its length onto either roller without binding.

24. A method according to claim 23, wherein rotating the control knob positioned on the shaft of the first roller in a first direction rotates the second roller to wind the film thereon via a one-way drive mechanism, and rotating said knob in the opposite direction rotates the first roller to align the film thereon without driving said second roller.

* * * * *